US00PP26714P2

(12) United States Plant Patent
Graff

(10) Patent No.: US PP26,714 P2
(45) Date of Patent: May 10, 2016

(54) ***HIBISCUS* PLANT NAMED 'MULTI TROPIC CHERISE'**

(50) Latin Name: *Hibiscus rosa-sinensis*
Varietal Denomination: Multi Tropic Cherise

(71) Applicant: Poul Graff, Sabro (DK)

(72) Inventor: Poul Graff, Sabro (DK)

(73) Assignee: Graff Breeding A/S, Sabro (DK)

( * ) Notice: Subject to any disclaimer, the term of this patent is extended or adjusted under 35 U.S.C. 154(b) by 105 days.

(21) Appl. No.: 14/120,536

(22) Filed: May 31, 2014

(51) Int. Cl.
*A01H 5/00* (2006.01)

(52) U.S. Cl.
USPC ..... Plt./257

(58) Field of Classification Search
USPC ..... Plt./257
See application file for complete search history.

*Primary Examiner* — Annette Para
(74) *Attorney, Agent, or Firm* — C. A. Whealy

(57) ABSTRACT

A new and distinct cultivar of *Hibiscus* plant named 'Multi Tropic Cherise', characterized by its upright, uniformly mounding and bushy plant habit; shiny dark green-colored leaves; uniform, continuous and freely flowering habit; red purple-colored flowers with dark red-colored centers; and good flower longevity.

2 Drawing Sheets

Botanical designation: *Hibiscus rosa-sinensis.*
Cultivar denomination: 'MULTI TROPIC CHERISE'.

BACKGROUND OF THE INVENTION

The present invention relates to a new and distinct cultivar of *Hibiscus* plant, botanically known as *Hibiscus rosa-sinensis,* and hereinafter referred to by the name 'Multi Tropic Cherise'.

The new *Hibiscus* plant is a product of a planned breeding program conducted by the Inventor in Sabro, Denmark. The objective of the breeding program is to create new compact, uniform, strong and freely-branching *Hibiscus* plants with continuous flowering and attractive long-lasting flowers.

The new *Hibiscus* plant originated from a cross-pollination conducted by the Inventor in October, 2006 in Sabro, Denmark of *Hibiscus rosa-sinensis* 'Camaro Wind', not patented, as the female, or seed, parent with a proprietary selection of *Hibiscus rosa-sinensis* identified as code number 2006-0001, not patented, as the male, or pollen, parent. The new *Hibiscus* plant was discovered and selected by the Inventor as a flowering plant within the progeny of the stated cross-pollination in a controlled greenhouse environment in Sabro, Denmark in August, 2007.

Asexual reproduction of the new *Hibiscus* plant by vegetative terminal cuttings in a controlled greenhouse environment in Sabro, Denmark since October, 2007 has shown that the unique features of this new *Hibiscus* plant are stable and reproduced true to type in successive generations.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Multi Tropic Cherise'. These characteristics in combination distinguish 'Multi Tropic Cherise' as a new and distinct *Hibiscus* plant:

1. Upright, uniformly mounding and bushy plant habit.
2. Shiny dark green-colored leaves.
3. Uniform, continuous and freely flowering habit.
4. Red purple-colored flowers with dark red-colored centers.
5. Good flower longevity.

Plants of the new *Hibiscus* can be compared to plants of the female parent, 'Camaro Wind'. Plants of the new *Hibiscus* differ primarily from plants of 'Camaro Wind' in the following characteristics:

1. Plants of the new *Hibiscus* have flatter flowers than plants of 'Camaro Wind'.
2. Plants of the new *Hibiscus* and 'Camaro Wind' differ in flower color as plants of 'Camaro Wind' have red-colored flowers.
3. Flowers of plants of the new *Hibiscus* are longer-lasting than flowers of plants of 'Camaro Wind'.

Plants of the new *Hibiscus* can be compared to plants of the male parent selection. Plants of the new *Hibiscus* differ primarily from plants of the male parent selection in the following characteristics:

1. Plants of the new *Hibiscus* have smaller flowers than plants of the male parent selection.
2. Plants of the new *Hibiscus* and the male parent selection differ in flower color as plants of the male parent selection have pink-colored flowers.
3. Flowers of plants of the new *Hibiscus* are not as long-lasting as flowers of the male parent selection.

Plants of the new *Hibiscus* can be compared to plants of the *Hibiscus rosa-sinensis* 'Adonis', disclosed in U.S. Plant Pat. No. 21,592. In side-by-side comparisons conducted in Sabro, Denmark, plants of the new *Hibiscus* differed from plants of 'Adonis' in the following characteristics:

1. Plants of the new *Hibiscus* and 'Adonis' differed in leaf shape.
2. Plants of the new *Hibiscus* and 'Adonis' differed in flower color as plants of 'Adonis' had dark pink-colored flowers.

3. Flowers of plants of the new *Hibiscus* were not as long-lasting as flowers of plants of 'Adonis'.

Plants of the new *Hibiscus* can be compared to plants of the *Hibiscus rosa-sinensis* 'Juno', disclosed in U.S. Plant patent application Ser. No. 13/694,674. In side-by-side comparisons conducted in Sabro, Denmark, plants of the new *Hibiscus* differed from plants of 'Juno' in the following characteristics:

1. Plants of the new *Hibiscus* and 'Juno' differed in leaf shape.
2. Plants of the new *Hibiscus* had smaller flowers than plants of 'Juno'.
3. Plants of the new *Hibiscus* and 'Juno' differed in flower color as plants of 'Juno' had lighter red purple-colored flowers.
4. Flowers of plants of the new *Hibiscus* were not as long-lasting as flowers of plants of 'Juno'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet comprises a side perspective view of a typical flowering plant of 'Multi Tropic Cherise' grown in a container.

The photograph on the second sheet is a close-up view of typical developing flower buds and a typical open flower of 'Multi Tropic Cherise'.

DETAILED BOTANICAL DESCRIPTION

The aforementioned photographs and following observations, measurements and values describe plants grown during the autumn and winter in 13-cm containers in a glass-covered greenhouse in Sabro, Denmark and under cultural practices typical of commercial *Hibiscus* production. During the production of the plants, day temperatures ranged from 20° C. to 25° C., night temperatures ranged from 19° C. to 21° C. and light levels ranged from 40 to 50 klux. Plants were pinched one time about nine to ten weeks after planting. Plants were 28 weeks old when the photographs and the description were taken. In the description, color references are made to The Royal Horticultural Society Colour Chart, 2001 Edition, except where general terms of ordinary dictionary significance are used.

Botanical classification: *Hibiscus rosa-sinensis* 'Multi Tropic Cherise'.

Parentage:

*Female, or seed, parent.*—*Hibiscus rosa-sinensis* 'Camaro Wind', not patented.

*Male or pollen parent.*—Proprietary selection of *Hibiscus rosa-sinensis* identified as code number GB 2006-0001, not patented.

Propagation:

*Type.*—By vegetative terminal cuttings.

*Time to initiate roots, summer.*—About four weeks at temperatures about 24° C.

*Time to initiate roots, winter.*—About five weeks at temperatures about 24° C.

*Time to produce a rooted young plant, summer.*—About nine weeks at temperatures about 24° C.

*Time to produce a rooted young plant, winter.*—About ten weeks at temperatures about 24° C.

*Root description.*—Medium in thickness, fleshy; color, close to 158A.

*Rooting habit.*—Freely branching; dense.

Plant description:

*Plant and growth habit.*—Upright, uniformly mounding and bushy plant habit; moderately vigorous growth habit.

*Branching habit.*—Freely branching habit with usually about four to six lateral branches developing per plant; pinching enhances lateral branch development.

*Plant height.*—About 35 cm to 55 cm.

*Plant diameter* (*area of spread*).—About 30 cm to 50 cm.

Lateral branch description:

*Length.*—About 15 cm to 25 cm.

*Diameter.*—About 3 mm to 7 mm.

*Internode length.*—About 1 cm to 5 cm.

*Strength.*—Strong.

*Texture.*—Smooth, glabrous; with development, becoming woody.

*Color, developing.*—Close to 146A.

*Color, developed.*—Close to N199A and 200A.

Leaf description:

*Arrangement.*—Alternate, single; numerous.

*Length.*—About 9 cm to 11 cm.

*Width.*—About 8 cm to 10 cm.

*Shape.*—Broadly ovate.

*Apex.*—Acuminate to cuspidate.

*Base.*—Obtuse.

*Margin.*—Towards the apex, irregularly serrate; towards the base, entire.

*Texture, upper surface.*—Smooth, glabrous; venation, recessed.

*Texture, lower surface.*—Slightly pubescent; venation, prominent.

*Luster, upper surface.*—Very glossy.

*Luster, lower surface.*—Glossy.

*Venation pattern.*—Pinnate; arcuate.

*Color.*—Developing leaves, upper surface: Close to 146A and 147A. Developing leaves, lower surface: Close to 146A to 146B. Fully expanded leaves, upper surface: Close to 139A; venation, close to 146A. Fully expanded leaves, lower surface: Close to 146A and 147A; venation, close to 146B to 146C.

*Petioles.*—Length: About 4 cm to 6 cm. Diameter: About 2 mm. Texture, upper and lower surfaces: Pubescent. Color, upper surface: Close to 147A. Color, lower surface: Close to 146A.

Flower description:

*Flower arrangement.*—Flowers arranged singly at terminal leaf axils; uniform, continuous and freely flowering habit with numerous flower buds and open flowers per plant at one time; flowers face mostly upright to slightly outwardly.

*Fragrance.*—None detected.

*Natural flowering season.*—Plants flower in the garden during the spring and summer or during periods of warm weather; in the greenhouse, plants can be flowered year-round; plants begin flowering about 10 to 18 weeks after pinching.

*Flower longevity.*—Good flower longevity, flowers last about two days on the plant; flowers persistent.

*Flower diameter.*—About 13 cm to 15 cm.

*Flower length* (*height*).—About 7 cm to 9 cm.

*Flower buds.*—Length: About 6 cm to 8 cm. Diameter: About 2 cm to 3 cm. Shape: Ovate to elliptical. Color: Close to 59A.

*Petals.*—Arrangement: Five imbricate petals in a single whorl. Length: About 8 cm. Width: About 6 cm. Shape: Fan-shaped. Apex: Rounded. Base: Attenuate. Margin: Entire, slightly undulate. Texture, upper surface: Glabrous, rugose; venation, slightly prominent. Texture, lower surface: Glabrous, rugose; venation, prominent. Luster, upper and lower surfaces: Matte. Color: When opening, upper surface: Close to 59B; towards the base, close to 53A. When opening, lower surface: Close to 59A. Fully opened, upper surface: Close to 59C; towards the base, close to 53A; venation, close to N59C; with development, main color becoming closer to 59B. Fully opened, lower surface: Close to 60A; venation, close to 60B; color does not change with development.

*Sepals.*—Appearance: Five sepals fused into a campanulate-shaped calyx. Length: About 2.5 cm to 3 cm. Width: About 1 cm to 1.3 cm. Shape: Lanceolate. Apex: Acuminate. Margin: Entire. Texture, upper surface: Rugose, pubescent; venation, prominent. Texture, lower surface: Slightly pubescent; venation, recessed. Luster, upper surface: Matte. Luster, lower surface: Slightly glossy. Color, upper surface: Close to 144A. Color, lower surface: Close to 143C.

*Peduncles.*—Length: About 4 cm to 5 cm. Diameter: About 2 mm to 3 mm. Strength: Strong. Texture: Sparsely pubescent. Color: Close to 146A.

*Reproductive organs.*—Androecium: Stamen number: Numerous, about 100. Staminal column length: About 7 cm. Staminal column color: Towards the base, close to 53A; mid-section, close to 60A; and towards the apex, close to 60B. Filament length: About 2.5 mm to 3 mm. Filament color: Close to 60B. Anther shape: Ovate, rounded. Anther length: About 1 mm to 2 mm. Anther color: Close to 19A. Amount of pollen: Abundant. Pollen color: Close to 17B. Gynoecium: Pistil length (including staminal column): About 8 cm to 9 cm. Style texture: Smooth, waxy. Style color: Close to 11D. Stigma appearance: Five-parted, rounded. Stigma color: Close to 58B. Ovary color: Close to 145A.

*Seeds and fruits.*—Seed and fruit development have not been observed on plants of the new *Hibiscus*.

Temperature tolerance: Plants of the new *Hibiscus* have been observed to have tolerate temperatures from about 1° C. to about 30° C.

Pathogen & pest resistance: Plants of the new *Hibiscus* have not been observed to be resistant to pathogens and pests common to *Hibiscus* plants.

It is claimed:

1. A new and distinct *Hibiscus* plant named 'Multi Tropic Cherise' as illustrated and described.

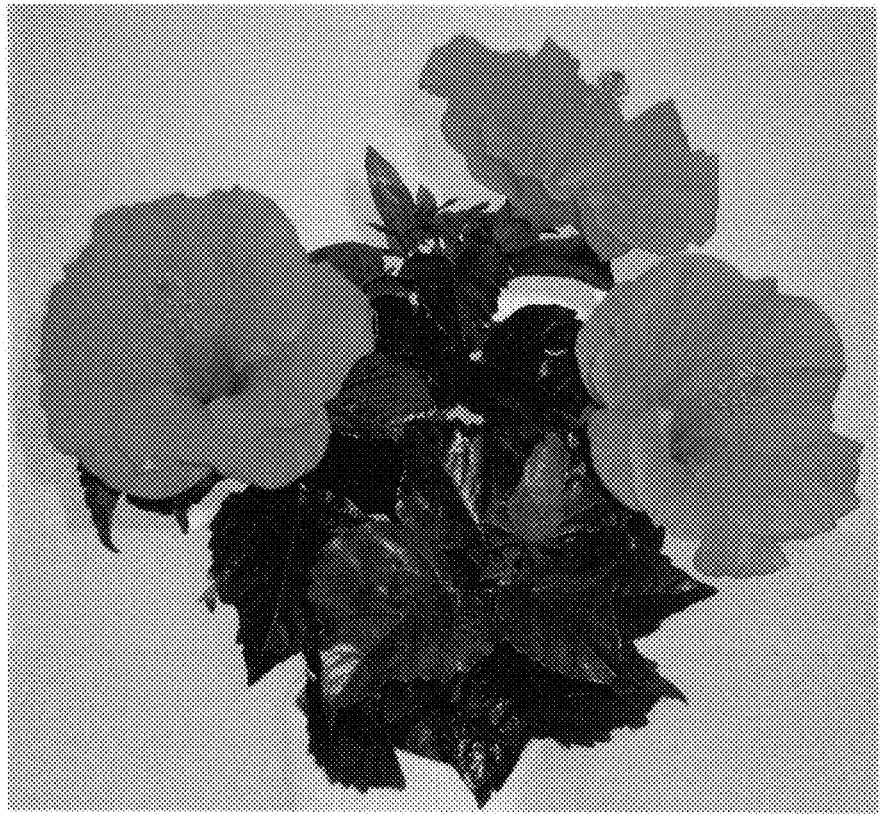

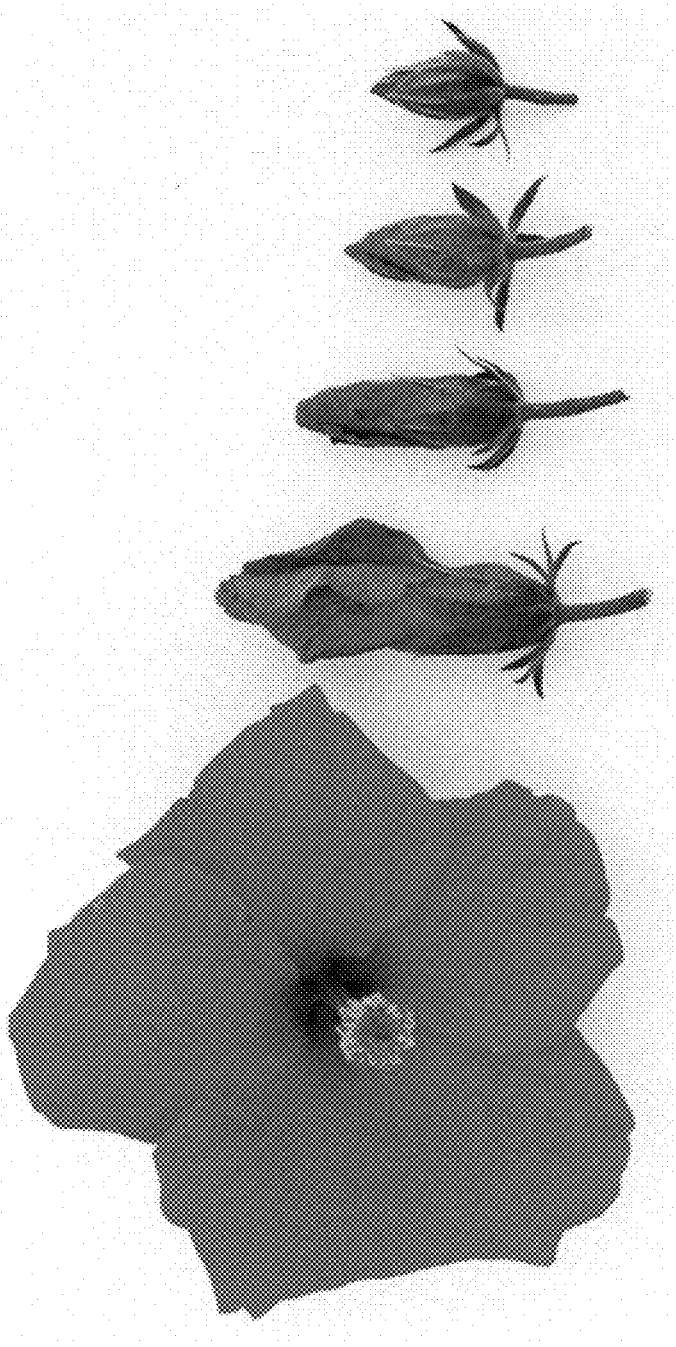

* * * * *